(12) United States Patent
Patek et al.

(10) Patent No.: US 10,869,617 B2
(45) Date of Patent: Dec. 22, 2020

(54) GAIT PATHOLOGY DETECTION AND MONITORING SYSTEM, AND METHOD

(71) Applicant: University of Virginia Patent Foundation, Charlottesville, VA (US)

(72) Inventors: Stephen D. Patek, Charlottesville, VA (US); Matthew M. Engelhard, Charlottesville, VA (US); John Lach, Charlottesville, VA (US); Myla D. Goldman, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 285 days.

(21) Appl. No.: 15/764,063

(22) PCT Filed: Sep. 28, 2016

(86) PCT No.: PCT/US2016/054200
§ 371 (c)(1),
(2) Date: Mar. 28, 2018

(87) PCT Pub. No.: WO2017/058927
PCT Pub. Date: Apr. 6, 2017

(65) Prior Publication Data
US 2018/0279914 A1  Oct. 4, 2018

Related U.S. Application Data

(60) Provisional application No. 62/233,836, filed on Sep. 28, 2015.

(51) Int. Cl.
*A61B 5/11* (2006.01)
*G06K 9/00* (2006.01)
*G06K 9/62* (2006.01)

(52) U.S. Cl.
CPC ............ *A61B 5/112* (2013.01); *G06K 9/0055* (2013.01); *G06K 9/00348* (2013.01); *G06K 9/00557* (2013.01); *G06K 9/6276* (2013.01); *A61B 2562/0219* (2013.01)

(58) Field of Classification Search
CPC ... A61B 5/11; A61B 5/112; A61B 2562/0219; G06K 9/00348
See application file for complete search history.

(56) References Cited

U.S. PATENT DOCUMENTS

2010/0191153 A1   7/2010  Sanders et al.
2011/0288811 A1*  11/2011 Greene ................ A61B 5/1038
                                                    702/141
2014/0235965 A1   8/2014  Tran
2015/0112603 A1   4/2015  Zhong
2018/0078179 A1*  3/2018  Deng ................... A61B 5/6898

OTHER PUBLICATIONS

Chen et al., "Affine and Regional Dynamic Time Warping," 2015, retrieved from the Internet; https://arxiv.org/pdf/1505.06531.pdf.

* cited by examiner

*Primary Examiner* — Thaddeus B Cox
(74) *Attorney, Agent, or Firm* — Potomac Law Group, PLLC; Vincent M De Luca

(57) ABSTRACT

A gait pathology detection and monitoring system, and method using rotation, scale, and offset invariant dynamic time warping (RSOI-DTW).

13 Claims, 15 Drawing Sheets

| | DTW | RSOI |
|---|---|---|
| # Correct (%) | 24 | 125 |
| | 19.2 | 100.0 |

*FIG. 2*

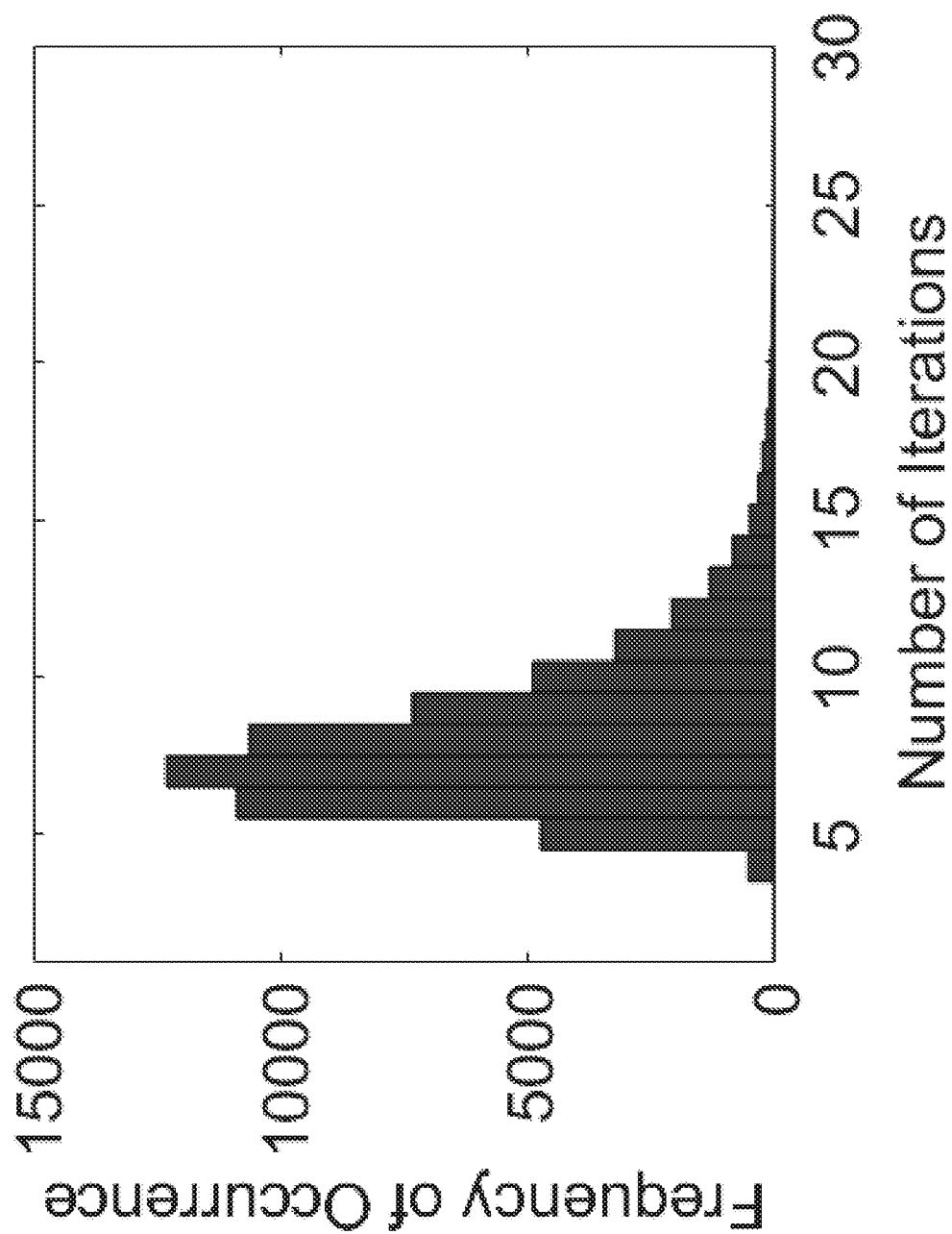

|  | Without Rotation | | With Rotation | |
| --- | --- | --- | --- | --- |
|  | DTW | RSOI | DTW | RSOI |
| # Correct (%) | 252<br>100.0 | 251<br>99.6 | 68<br>27.0 | 251<br>99.6 |

*FIG. 5*

| | DTW EER (%) | RSOI EER (%) |
|---|---|---|
| Mean | 0.0 | 0.5 |
| Median | 0.0 | 0.0 |
| Min | 0.0 | 0.0 |
| Max | 0.0 | 7.1 |

*FIG. 6*

|        | DTW EER (%) | RSOI EER (%) |
|--------|-------------|--------------|
| Mean   | 43.8        | 31.3         |
| Median | 50.0        | 39.6         |
| Min    | 0.0         | 0.0          |
| Max    | 52.3        | 50.0         |

*FIG. 9*

|          | DTW EER (%) | RSOI EER (%) |
|----------|-------------|--------------|
| Mean     | 4.9         | 8.0          |
| Median   | 0.0         | 1.1          |
| Min      | 0.0         | 0.0          |
| Max      | 31.3        | 33.3         |

*FIG. 11*

GAIT PATHOLOGY DETECTION AND MONITORING SYSTEM, AND METHOD

RELATED APPLICATION

This application claims priority to U.S. Provisional Patent Application entitled Toward Detection and Monitoring of Gait Pathology using Inertial Sensors under Rotation, Scale, and Offset Invariant Dynamic Time Warping, Application No. 62/233,836 filed on Sep. 28, 2015, which application is fully incorporated herein by reference.

FIELD

The present invention is directed to a gait pathology detection and monitoring system, and method using rotation, scale, and offset invariant dynamic time warping (RSOI-DTW).

BACKGROUND

Movement disorders, stroke, traumatic injury, and other pathologies can degrade walking ability. A patient's walking quality can be monitored by a care provider to guide treatment decisions, measure the effectiveness of interventions, or provide prognostic information to the patient. While personal activity tracking devices make it easy to measure the quantity of a person's walking, they are not yet equipped to measure and monitor its quality over time.

The pathology detection and monitoring problem is challenging because of heterogeneity among persons, pathologies, and devices. What is abnormal in one person might be typical in another, and two different pathologies (e.g. hemiparesis gait and Parkinsonian gait) may have little in common. Further, each personal tracking device has its own unique combination of sensors, placement location(s) on the body, and attachment method(s). If inertial signal features are used to monitor walking quality, this heterogeneity must be considered carefully. The features important in one scenario may not be important in others.

To overcome these difficulties, monitoring can be based on a similarity measure, not extracted features. In a similarity measure based strategy, rather than learning the unique set of features important for each combination of persons, pathologies, and devices, a monitoring algorithm can instead observe a person's walking at baseline, then monitor its similarity to current walking patterns as time goes on. No prior information about pathology is needed, and a person's unique walking characteristics are not a hindrance.

In rehabilitation following stroke or trauma, similarity to baseline should return as walking ability is recovered. In chronic, progressive disease, the similarity to baseline can be quantified on an ongoing basis, and new baselines can be established to detect further degradation. Current walking is compared only to baseline measurements from the same person using the same device, so observed differences may be attributed primarily to changing walking patterns.

Patients would routinely complete a self-initiated walking test at home, wearing a personal activity tracking device or smartphone capable of recording inertial data. Gait cycles from this test would then be compared to baseline cycles using an appropriate similarity measure. For this purpose, rotation, scale, and offset (RSO) invariant dynamic time warping (RSOI-DTW), a variant of the well-known dynamic time warping (DTW) algorithm, can be used.

DTW has been used successfully for activity recognition [10] and biometric gait recognition [4][9][11][13], and several variants have been proposed. Scale and offset invariant DTW, in which one sequence can be scaled or shifted to improve similarity, has been developed by several authors, notably Chen et al., who evaluated an iterative algorithm on a number of time series datasets [2]. When analyzing gait, scale and offset invariance may mitigate variability due to walking surface, shoe type, attachment method, and moderate changes in speed.

In addition to scale and offset invariance, RSOI-DTW incorporates rotation invariance, allowing it to match gait cycles regardless of device orientation. This is a necessity in a real world, self-testing scenario, because a particular orientation cannot be assumed. A rotation invariant DTW algorithm was used by Qiao and Yasuhara to analyze two dimensional handwriting samples [12], and Bours et al. have devised a rotation invariant algorithm based upon principal component analysis [1]. It appears that no iterative, rotation invariant DTW variant appropriate for three-dimensional inertial data has been developed and tested.

However, a number of methods for inertial data processing not based on DTW have incorporated rotation invariance. Chien et al. developed an algorithm that corrects sensor orientation as part of model-based classification of upper limb movements and walking activities [3]. Recently, Gong et al. developed a method for activity classification robust sensor mounting errors, including rotation, using a linear dynamical model based approach [6].

Inertial devices have been used for disability monitoring in many different contexts. The ISway test developed by Mancini et al. uses an accelerometer to measure postural sway resulting from neurological impairment [8]. Salarian et al. created the iTug system, which uses inertial sensors to partly automate the Timed Up and Go test, a clinical measure of balance and mobility [15]. Spain et al. captured differences between multiple sclerosis subjects grouped by disability level using features derived from inertial sensors, but could not detect changes in those features over time [16]. Many studies have used daily step counts derived from inertial sensors as an outcome measure, but comparatively few have assessed features intrinsic to individual gait cycles.

SUMMARY

The presently described subject matter is directed to an improved gait pathology detection and monitoring system and method.

The presently described subject matter is directed to an improved gait pathology detection and monitoring system and method using rotation, scale, and offset invariant dynamic time warping (RSOI-DTW).

The presently described subject matter is directed to a gait pathology detection and monitoring method, comprising or consisting of securing a personal activity tracking electronic device having an accelerometer onto a leg of a user; detecting gait movement of the user during walking using the personal activity tracking electronic device; generating gait data of the user from the detected gait movement of the user during walking; demonstrating at least one style of gait of the user when generating the gait data; processing the gait data using rotation, scale, and offset invariant dynamic time warping (RSOI-DTW) even in the presence of sensor rotation.

The presently described subject matter is directed to a gait pathology detection and monitoring method, comprising or consisting of securing a personal activity tracking electronic device having an accelerometer onto a leg of a user; detecting gait movement of the user during walking using the personal activity tracking electronic device; generating gait data of the user from the detected gait movement of the user during walking; demonstrating at least one style of gait of the user when generating the gait data; processing the gait data using rotation, scale, and offset invariant dynamic time warping (RSOI-DTW) even in the presence of sensor rotation, and further comprising processing the user's gait data using dynamic time warping (DTW)

The presently described subject matter is directed to a gait pathology detection and monitoring method, comprising or consisting of securing a personal activity tracking electronic device having an accelerometer onto a leg of a user; detecting gait movement of the user during walking using the personal activity tracking electronic device; generating gait data of the user from the detected gait movement of the user during walking; demonstrating at least one style of gait of the user when generating the gait data; processing the gait data using rotation, scale, and offset invariant dynamic time warping (RSOI-DTW) even in the presence of sensor rotation, further comprising processing the user's gait data using dynamic time warping (DTW), and further comprising comparing the results of the processing of the gait data using RSOI-DTW and DTW to determine any gait recognition problem.

The presently described subject matter is directed to a gait pathology detection and monitoring method, comprising or consisting of securing a personal activity tracking electronic device having an accelerometer onto a leg of a user; detecting gait movement of the user during walking using the personal activity tracking electronic device; generating gait data of the user from the detected gait movement of the user during walking; demonstrating at least one style of gait of the user when generating the gait data; processing the gait data using rotation, scale, and offset invariant dynamic time warping (RSOI-DTW) even in the presence of sensor rotation, further comprising processing the user's gait data using dynamic time warping (DTW), further comprising comparing the results of the processing of the gait data using RSOI-DTW and DTW to determine any gait recognition problem, and further comprising applying randomly chosen rotations to each test cycle beforehand.

The presently described subject matter is directed to a gait pathology detection and monitoring method, comprising or consisting of securing a personal activity tracking electronic device having an accelerometer onto a leg of a user; detecting gait movement of the user during walking using the personal activity tracking electronic device; generating gait data of the user from the detected gait movement of the user during walking; demonstrating at least one style of gait of the user when generating the gait data; processing the gait data using rotation, scale, and offset invariant dynamic time warping (RSOI-DTW) even in the presence of sensor rotation, further comprising applying gait recognition to the resulting gait data to determine whether a gait cycle of unknown origin belongs to the user.

The presently described subject matter is directed to a gait pathology detection and monitoring method, comprising or consisting of securing a personal activity tracking electronic device having an accelerometer onto a leg of a user; detecting gait movement of the user during walking using the personal activity tracking electronic device; generating gait data of the user from the detected gait movement of the user during walking; demonstrating at least one style of gait of the user when generating the gait data; processing the gait data using rotation, scale, and offset invariant dynamic time warping (RSOI-DTW) even in the presence of sensor rotation, further comprising determining whether a particular gait cycle represents the user's normal gait or a possible pathology.

The presently described subject matter is directed to a gait pathology detection and monitoring method, comprising or consisting of securing a personal activity tracking electronic device having an accelerometer onto a leg of a user; detecting gait movement of the user during walking using the personal activity tracking electronic device; generating gait data of the user from the detected gait movement of the user during walking; demonstrating at least one style of gait of the user when generating the gait data; processing the gait data using rotation, scale, and offset invariant dynamic time warping (RSOI-DTW) even in the presence of sensor rotation, further comprising demonstrating four different styles of gait by the user during detection, including casual walking, fast walking, ataxic walking, and right leg circumduction.

The presently described subject matter is directed to a gait pathology detection and monitoring method, comprising or consisting of securing a personal activity tracking electronic device having an accelerometer onto a leg of a user; detecting gait movement of the user during walking using the personal activity tracking electronic device; generating gait data of the user from the detected gait movement of the user during walking; demonstrating at least one style of gait of the user when generating the gait data; processing the gait data using rotation, scale, and offset invariant dynamic time warping (RSOI-DTW) even in the presence of sensor rotation, further comprising segmenting the user's gait data.

The presently described subject matter is directed to a gait pathology detection and monitoring method, comprising or consisting of securing a personal activity tracking electronic device having an accelerometer onto a leg of a user; detecting gait movement of the user during walking using the personal activity tracking electronic device; generating gait data of the user from the detected gait movement of the user during walking; demonstrating at least one style of gait of the user when generating the gait data; processing the gait data using rotation, scale, and offset invariant dynamic time warping (RSOI-DTW) even in the presence of sensor rotation, further comprising segmenting the user's gait data, wherein the user's gait data is segmented into gait cycles, defined as data between consecutive heel strikes of the user during detection.

The presently described subject matter is directed to a gait pathology detection and monitoring method, comprising or consisting of securing a personal activity tracking electronic device having an accelerometer onto a leg of a user; detecting gait movement of the user during walking using the personal activity tracking electronic device; generating gait data of the user from the detected gait movement of the user during walking; demonstrating at least one style of gait of the user when generating the gait data; processing the gait data using rotation, scale, and offset invariant dynamic time warping (RSOI-DTW) even in the presence of sensor rotation, further comprising measuring changes in walkability of the user by detecting changes by comparing the user's current gait cycles against prior baseline gait cycles.

The presently described subject matter is directed to a gait pathology detection and monitoring method, comprising or consisting of securing a personal activity tracking electronic device having an accelerometer onto a leg of a user; detecting gait movement of the user during walking using the personal activity tracking electronic device; generating gait data of the user from the detected gait movement of the user during walking; demonstrating at least one style of gait of the user when generating the gait data; processing the gait data using rotation, scale, and offset invariant dynamic time warping (RSOI-DTW) even in the presence of sensor rotation, further comprising measuring changes in walkability of the user by detecting changes by comparing the user's current gait cycles against prior baseline gait cycles, wherein monitoring the user's walkability is measured on an ongoing basis.

The presently described subject matter is directed to a gait pathology detection and monitoring system, comprising or consisting of a personal activity tracking electronic device having an accelerometer, the personal activity tracking electronic device configured to fit onto a leg of a user, the personal activity tracking electronic device configured to detect the gait movement of the user when walking and generate gait data of the user; and an electronic apparatus configured to receive the generated gait data of the user and processing the gait data using rotation, scale, and offset (RSO) invariant dynamic time warping (RSOI-DTW) even in the presence of sensor rotation.

The presently described subject matter is directed to a gait pathology detection and monitoring system, comprising or consisting of a personal activity tracking electronic device having an accelerometer, the personal activity tracking electronic device configured to fit onto a leg of a user, the personal activity tracking electronic device configured to detect the gait movement of the user when walking and generate gait data of the user; and an electronic apparatus configured to receive the generated gait data of the user and processing the gait data using rotation, scale, and offset (RSO) invariant dynamic time warping (RSOI-DTW) even in the presence of sensor rotation, wherein the electronic apparatus comprises a processor, a graphic processing unit, a memory, and a bus connected to the processor, the graphic processing unit, the memory to allow communication therebetween.

Walking ability can be degraded by a number of pathologies, including movement disorders, stroke, and injury. A personal activity tracking device can gather inertial data needed to measure walking quality. To detect changes in walking ability, the similarity between a person's current gait cycles and their known baseline gait cycles may be measured on an ongoing basis. This strategy requires a similarity measure robust to sources of variability encountered in an outpatient scenario, including changes in walking surface, walking speed, and sensor orientation. Here we propose rotation, scale, and offset invariant dynamic time warping (RSOI-DTW), a variant of the well-known dynamic time warping (DTW) algorithm, as a generalization of DTW appropriate for three-dimensional inertial data. RSOI-DTW is invariant under rotation, scaling, and offset, yet it preserves the salient features of gait cycles required for gait monitoring. To support this claim, gait cycles from 21 subjects walking with four different styles were compared using both DTW and RSOI-DTW. The data shows that RSOI-DTW converges quickly and achieves rotation, scale, and offset invariance. Both algorithms distinguish persons and detect abnormal walking, but only RSOI-DTW does so in the presence of sensor rotation. Variations in walking speed pose a challenge for both algorithms, but performance is improved by collecting baseline information at a variety of speeds.

BRIEF DESCRIPTION OF DRAWINGS

FIG. 2 is a table showing that RSOI-DTW achieves perfect 1NN recognition of cycles collected with the sensor incorrectly oriented. This table shows the number of cycles correctly classified under DTW and RSOI-DTW distances out of the 125 cycles collected from three subjects.

FIGS. 4a and 4B are graphical illustrations showing that RSOI-DTW converges after 8 iterations on average. These figures show histograms of the number of iterations required to compare pairs of cycles.

FIG. 5 is a table showing that Table 2: 1NN classification of casual gait is almost perfect under both DTW and RSOI-DTW. However, when rotations are applied to individual cycles beforehand, only RSOI-DTW succeeds. This table shows the number of cycles correctly recognized out of the 252 tested.

FIG. 6 is a table showing that threshold-based gait recognition achieves an equal error rate (EER) of zero in all subjects under DTW, and all but four subjects under RSOI-DTW. This table summarizes the EER for the decision problem in all subjects.

FIG. 9 is a table showing that Fast gait is hard to distinguish from pathology using the casual gait cycles as templates. This table summarizes the equal error rate (EER) in all subjects when distinguishing normal gait (fast or slow) from simulated pathology.

FIG. 11 is a table showing that including fast gait cycles in the template set dramatically improves performance when distinguishing normal gait from simulated pathology. This table summarizes the improved equal error rate (EER) in all subjects.

DETAILED DESCRIPTION

Data Collection and Segmentation

Figure 1A:
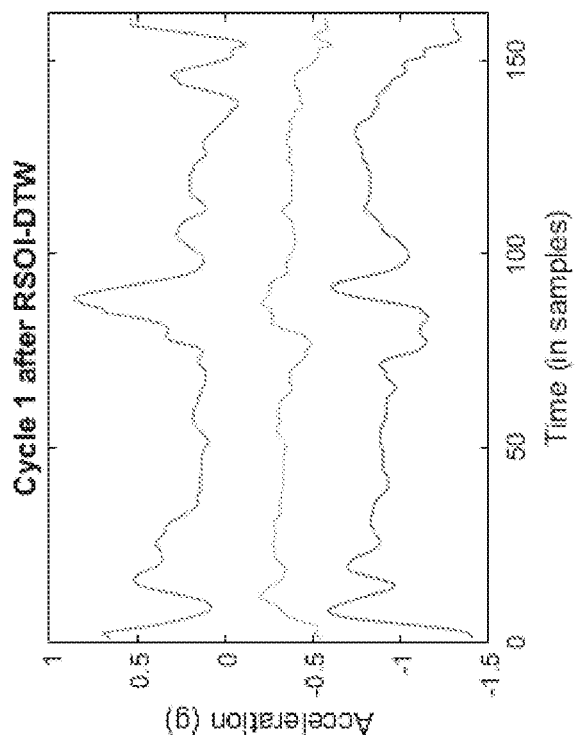
FIGS. 1A-1F are graphical illustrations showing that RSOI-DTW is rotation, scale, and offset invariant: when a randomly chosen RSO transformation is applied to cycle 2 (FIG. 1E), the RSOI-DTW algorithm corrects it (FIG. 1F).

The data collection and segmentation can be performed according to the following description.

Twenty-one (21) subjects participated in a walking trial. The subjects wore a single ActiGraph accelerometer on their left hip, secured using an elastic belt with a pouch for the device. All subjects wore the same device. Each subject was asked to walk down a long corridor four times to demonstrate four different styles of gait: casual walking, fast walking, ataxic walking, and right leg circumduction.

Ataxic walking is seen in persons with balance difficulties, characterized by a widebase and lateral swaying. Circumduction is the outward, circular swinging of one leg during its swing phase. It occurs when the leg is rigid or spastic at the knee and/or ankle joint.

The subjects each walked with each style in one direction for 40 steps, then turned, paused five seconds, and walked back with the next style. Each style was demonstrated before the trial, and subjects were given an opportunity to practice until comfortable.

Three subjects completed an additional trial in which they walked casually each time, but with four different sensor orientations.

The data was manually divided by person and walking style and segmented into gait cycles, defined as the data between consecutive left heel strikes. There are prominent peaks in the accelerometer signal at the point of heel strike in all walking styles, making the heel strikes easy to identify. Subsequent processing using DTW and RSOI-DTW exploits these gait cycles.

Dynamic Time Warping

The individual gait cycles were compared using DTW and RSOI-DTW, the variant of DTW described in the next section. Here we offer a brief, formal description of the DTW algorithm. A more comprehensive treatment may be found in [7].

The DTW algorithm takes two sequences $X=(x_1, \ldots, x_m)$ and $Y=(y_1, \ldots, y_n)$ as inputs and returns a measure of similarity $d_{DTW}$, often called the DTW distance, between them. In this work, the $x_i$ and $y_i$ are three dimensional acceleration vectors, but in general they may be vector or scalar valued. Our implementation of DTW also returns warped sequences $X_W$ and $Y_W$ derived from X and Y by (possibly) repeating individual terms to improve alignment. More precisely, $X_W=((x_1)^{a1}, \ldots, (x_m)^{am})$ and $Y_W=((y_1)^{b1}, \ldots, (y_n)^{bn})$, where $(.)^k$ denotes k repetitions of a term, and the $a_j$ and $b_j$ are positive integers found by the algorithm. Using this notation, the DTW distance $d_{DTW}$ is the squared Euclidean distance between $X_W$ and $Y_W$, defined as follows:

Definition 1. Given sequences $A=(a_1, \ldots, a_N)$ and $B=(b_1, \ldots, b_N)$, the squared Euclidean distance between A and B is:

$$d(A, B) = \sum_{i=1}^{N} \|a_i - b_i\|^2 \quad (1)$$

where $\|\cdot\|$ is the usual Euclidean norm.

To compute $d_{DTW}$, $X_W$, and $Y_W$, we first construct an (m×n) matrix D, where $D_{(i,j)}=\|x_i-y_j\|^2$. Intuitively, we then find the minimum cost path through D from $D_{(1,1)}$ to $D_{(m,n)}$ subject to a path constraint. Letting $w_k$ be the $k^{th}$ element of a warping path W—a possible path through D—we constrain W to allow only three moves: repeat the current point in X, repeat the current point in Y, or move to the next point in both. Formally, if $w_k=(i_k, j_k)$, then $w_{k+1} \in \{(i_k+1, j_k), (i_k+1, j_k+1), (i_k, j_k+1)\}$. The optimal path from (i, j) to (m, n) and its associated cost $C_{(i,j)}$ are computed using dynamic programming, where $C_{(m,n)}=D_{(m,n)}$, and the remaining $C_{(i,j)}$ are given by the following recursion:

$$C_{(i,j)}=D_{(i,j)}+\min\{C_{(i+1,j)}, C_{(i+1,j+1)}, C_{(i,j+1)}\} \quad (2)$$

This recursion may be carried out row-wise or column-wise, with $C_{(i,j)}=\infty$ for i>m or j>n. The final DTW distance is $C_{(1,1)}$, and the warping path W along with the warped sequences $X_W$ and $Y_W$ may be recovered from C.

In this work, the sequence Y is resampled to be the same length as X. Further, the warping path is limited to the Sakoe-Chiba band [14] to reduce computation, so that $C_{(i,j)}=\infty$ whenever $|j-i|$ is greater than one fourth the length of the input sequences.

Rotation, Scale, and Offset Invariant DTW

RSOI-DTW is an iterative algorithm that alternates between optimizing the rotation, scaling, and offset of the sequence Y, and optimizing the warping path using DTW. The former optimization is an instance of the Procrustes problem, which may be solved in closed form using singular value decomposition. The details of this problem are beyond the current scope, but may be found in [5].

In our version of the Procrustes problem, the rotation matrices are limited to SO(3), the (3×3) orthogonal matrices of determinant 1. SO(3) are the rigid rotations in $\mathbb{R}^3$, excluding reflection; they correspond with the set of rotations possible for a rigid physical object. These matrices form a group: in particular, they are invertible, where the inverse is also a rigid rotation, and the product of two rigid rotations is a rigid rotation. This section first defines the transformations allowed in RSOI-DTW—the RSO transformations—then provides the RSOI-DTW algorithm. Finally, it proves that RSOI-DTW is rotation, scale, and offset invariant under typical circumstances, and the algorithm is guaranteed to terminate.

DEFINITION 2. An RSO transformation is an affine transformation $f: \mathbb{R}^3 \to \mathbb{R}^3$ of the form $f(x)=sRx+b$, where $s \in \mathbb{R}^+$, $R \in SO(3)$, and $b \in \mathbb{R}^3$.

PROPOSITION 1. The RSO transformations are closed under composition and inverse, thus forming a subgroup of the affine group.

PROOF.

Let $\frac{1}{s_\alpha}(R_\alpha)^{-1} b_\alpha f_\alpha(x) = s_\alpha R_\alpha x + b_\alpha$, and $f_\beta(x)=s_\beta R_\beta x+b_\beta$. The inverse of $f_\alpha$ is given by $$(f_\alpha)^{-1}(x) = \frac{1}{s_\alpha}(R_\alpha)^{-1}x - \frac{1}{s_\alpha}(R_\alpha)^{-1}b_\alpha.$$

By inspection, $$\frac{1}{s_\alpha} \in \mathbb{R}^+$$

and $$-\frac{1}{s_\alpha}(R_\alpha)^{-1}b_\alpha \in \mathbb{R}^3,$$

and $(R_\alpha)^{-1} \in SO(3)$ because $SO(3)$ is closed under inverse. Thus the RSO transformations are closed under inverse.

The composition of $f_\alpha$ and $f_\beta$ is given by $(f_\alpha \bigcirc f_\beta)(x) = (s_\alpha s_\beta)(R_\alpha R_\beta)x + (s_\alpha R_\alpha b_\beta + b_\alpha)$. As before, we note that $s_\alpha s_\beta \in \mathbb{R}^+$ and $(s_\alpha R_\alpha b_\beta + b_\alpha) \in \mathbb{R}^3$; and the closure of $SO(3)$ under composition guarantees that $R_\alpha R_\beta \in SO(3)$. Thus the RSO transformations are closed under composition.

DEFINITION 3. Given an RSO transformation f and a sequence $X = (x_1, \ldots, x_n)$, where $x_i \in \mathbb{R}^3 \forall i$, the sequence $f(X)$ is defined to be $(f(x_1), \ldots, f(x_n))$.

Having covered the necessary background information, we now present the RSOI-DTW algorithm.

ALGORITHM 1. Rotation, Scale, and Offset Invariant DTW

```
 1: procedure RSOI-DTW (X, Y )
 2:    X_W ← X
 3:    Y_W ← Y
 4:    d ← ∞
 5:    repeat
 6:       d_old ← d
 7:       f* ← argmin d(X_W, f(Y_W))
 8:                ▷ where f is an RSO transformation
 9:       (d, X_W, Y_W) ← DTW (X, f*(Y))
10:    until (d_old − d) < ε
11:    return d, X_W, f(Y_W)
12: end procedure
```

This algorithm can be restricted for a particular use case by limiting f to a subset of the RSO transformations. If rotation is not a concern, R may be held to I, the identity matrix, reducing RSOI-DTW to scale and offset invariant DTW, as developed in [2]. Similarly, if scaling is not a concern, s may be held to 1.

PROPOSITION 2. RSOI-DTW is rotation, scale, and offset invariant. More precisely, let X, Y, and Z be sequences in $\mathbb{R}^3$ of equal length, where $Z = f_z(Y)$ for some RSO transformation $f_z$. If $d(f(Z_W), X_W)$ has a unique minimizer $f^*$ at each iteration of the RSOI-DTW algorithm, then RSOI-DTW (X, Y) = RSOI-DTW(X, Z).

PROOF. Let $f_z$ be the RSO transformation taking Y to Z, so that $fz(Y) = Z$, and suppose $fz(YW) = Z_w$ at the beginning of the $i^{th}$ iteration of RSOI-DTW(X, Y) and RSOI-DTW(X,Z). We proceed by induction; note that the i=1 case holds, since we initialize $Y_W \leftarrow Y$ and $Z_W \leftarrow Z$.

Given a unique RSO transformation $f^*$ that minimizes $d(f(Z_W), X_w)$ in iteration i, the RSO transformation $(f^* \bigcirc f_z)$ must be the unique minimizer of $d(f(YW), X_W)$. To see this, suppose there were some other RSO transformation g such that $d(g(Y_w), X_W) \leq d((f^* \bigcirc f_z)(Y_W), X_W)$. Since $Y^W = f_z^{-1}(Z_W)$, where $f_z^{-1}$ is the inverse of $f_z$, we have:

$$d((g \cdot f_z^{-1})(Z_w), X_w) = d((g(f_z^{-1}(Z_W)), X_W)$$
$$= d(g(Y_W), X_W)$$
$$\leq d((f^* \cdot f_z)(Y_W), X_W)$$
$$= d((f^*(f_z(Y_W)), X_W)$$
$$= d(f^*(Z_W), X_W),$$

violating our assumption that $f^*$ is the unique minimizer.

Knowing that $f^*$ and $(f^* \bigcirc f_z)$ are the unique minimizers found in line 7 of the ith iteration of RSOI-DTW(X,Z) and RSOI-DTW(X,Y), respectively, we conclude that the input to the DTW subroutine is $f^*(Z_W)$ in either case. Because of this, DTW returns the same distance d and warping path W in both cases, guaranteeing $f_z(Y_W) = Z_W$ at the beginning of the $(i+1)^{th}$ iteration, completing our inductive proof.

Intuitively, since the first step in RSOI-DTW is to optimally rotate, scale, and shift the input, the sequences $Y_W$ and $Z_W$ are both transformed to $f^*(Z_W)$ in the first iteration of the algorithm, and subsequent processing is identical.

Proposition 3. RSOI-DTW terminates.

Proof. First, notice that $f(X)_W = f(X)_W$, because applying the warping path W is simply a repetition of terms, and the transformation f is applied once to each term in either case.

Let $d_i$, $W_i$, and $f_i$ be the distance, warping path, and transformation found in iteration i, so that $d_i = d(X_{Wi}, f_i(Y)_{Wi})$. In iteration (i+1), $f_{i+1}$ is chosen to minimize $d(X_{Wi}, f(Y)_{Wi})$, thus $d(X_{Wi}, f_i+1(Y)w_i) \leq d_i$. And DTW find the warping path $W_{i+1}$ minimizing $d(X, f_i+1(Y))$. Together, we have:

$$d_{i+1} = d(X_{W_{i+1}}, f_{i+1}(Y)_{W_{i+1}}) \leq d(X_{W_i}, f_{i+1}(Y)_{W_i}) \leq d_i.$$

Since this holds for all i, the sequence $\{d_i\}_{i \in} \{d_i\}_{i \in \mathbb{N}}$ is monotonically decreasing. Further, since the $d_i$ are squared Euclidean distances, they are bounded below by zero. Therefore this sequence converges by the monotone convergence theorem, guaranteeing termination of the RSOI-DTW algorithm.

Convergence and RSO Invariance of RSOIDTW in Practice

Having established the theoretical properties of RSOI-DTW in the previous section, it is shown that it performs as expected on the walking dataset.

FIG. 1 illustrates the use of RSOI-DTW to compare two gait cycles. These cycles were both taken from the casual walking portion of the trial in the same subject. The raw cycles C1 and C2, labeled "Cycle 1" and "Cycle 2", are shown in FIG. 1A and FIG. 1C, respectively. FIG. 1E shows cycle two after application of a randomly chosen RSO transformation f. The plots in FIGS. 1B, 1D, and 1F show how these plots are altered by RSOI-DTW. When running RSOI-DTW(C1;C2), the plots in FIGS. 1B and 1D are returned: the plot in FIG. 1B is the warped version of C1, and the plot in FIG. 1D is the warped, transformed version of C2. Here the rotation, scale, and offset are small, because sensor alignment was consistent, and no rotation was applied. When running RSOI-DTW(C1; f(C2)), the same two plots are returned.

Figure 1B:
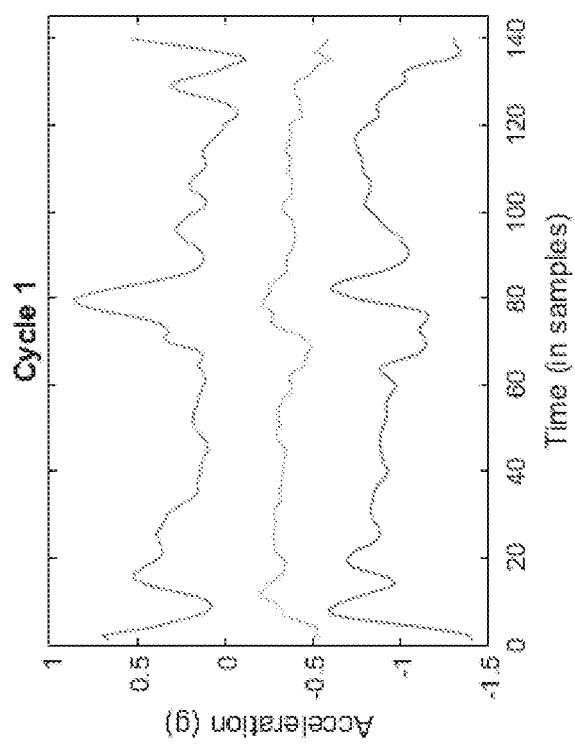
Figure 1C:
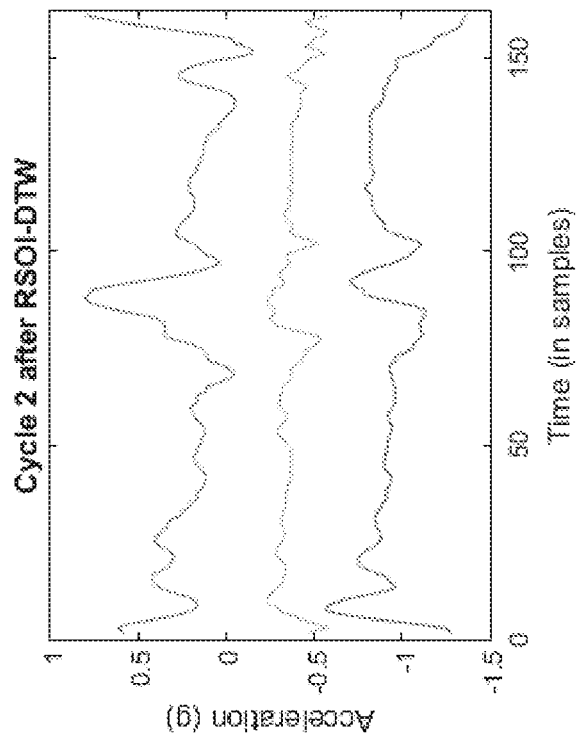
Figure 1D:
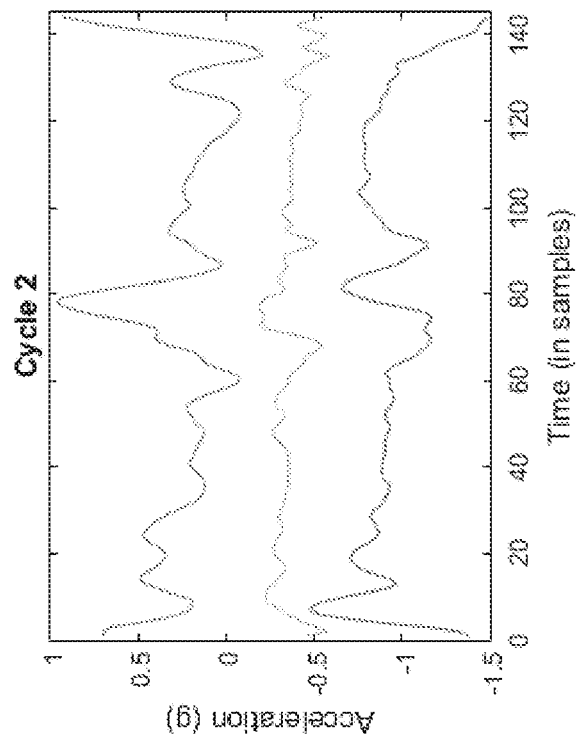
Figure 1F:
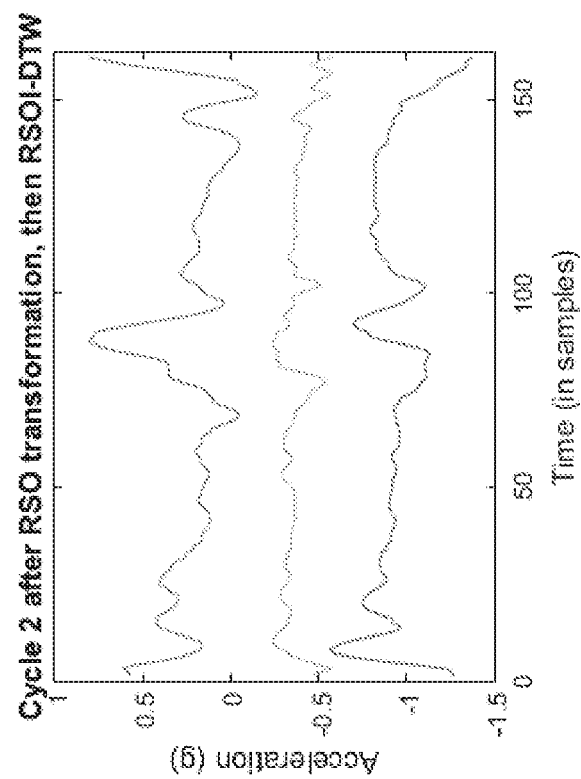
Figure 1E:
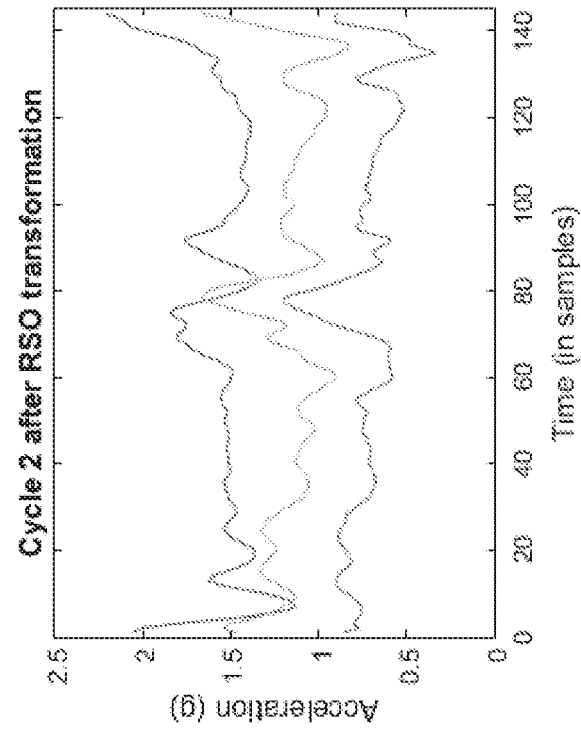

The warped version of C1 is not shown, because it is identical to the plot in FIG. 1B. The warped, rotated version of f(C2) is shown in plot of FIG. 1F for emphasis. This plot is identical to the plot shown in FIG. 1D, because RSOI-DTW is invariant under the RSO transformation f.

To confirm this result in a large sample, a randomly chosen RSO transformation was applied to each of our 21 participants' 12 casual gait cycles. RSOI-DTW was then used to compare the transformed cycles to all of the original, non-transformed cycles, for a total of 252, or 31,626, comparisons. The resulting distances were compared to the corresponding distances obtained without first applying a transformation. In each of these 31,626 cases, the RSOI-DTW distances were identical up to rounding error, never differing by more than $10^{-13}$.

Figure 2:
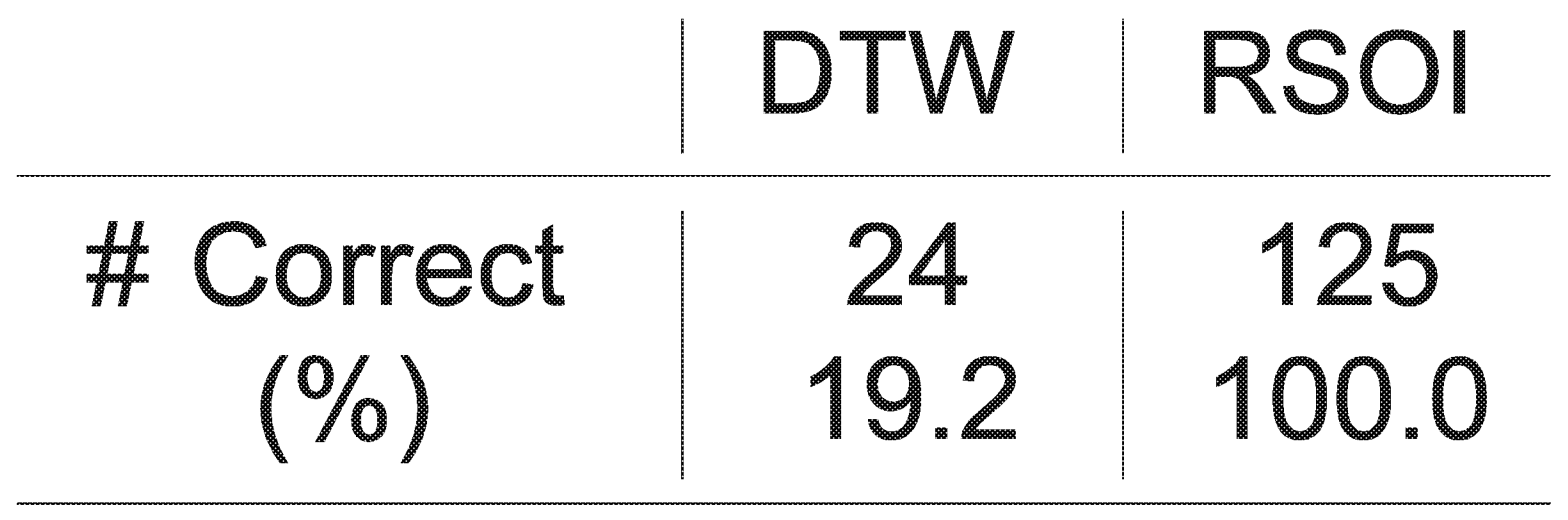
Figure 3A:
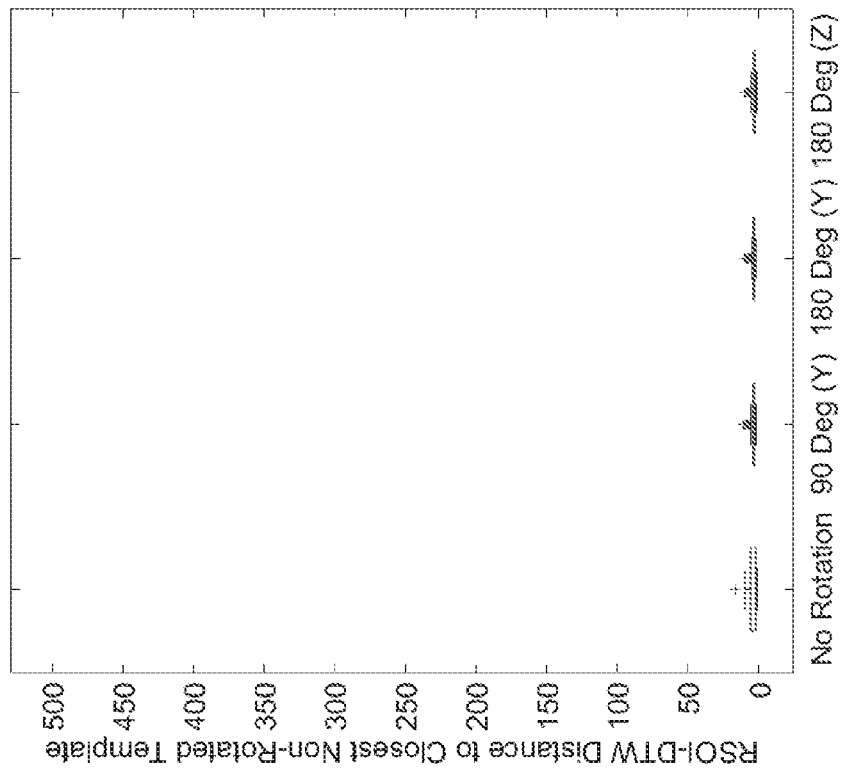
FIGS. 3A and 3B are graphical illustrations showing that RSOI-DTW distances are similar regardless of sensor orientation. The graphs show DTW distances (FIG. 3A) and RSOI-DTW distances (FIG. 3B) between three sets of incorrectly oriented cycles and correctly oriented cycles from the same subject.
Figure 3B:
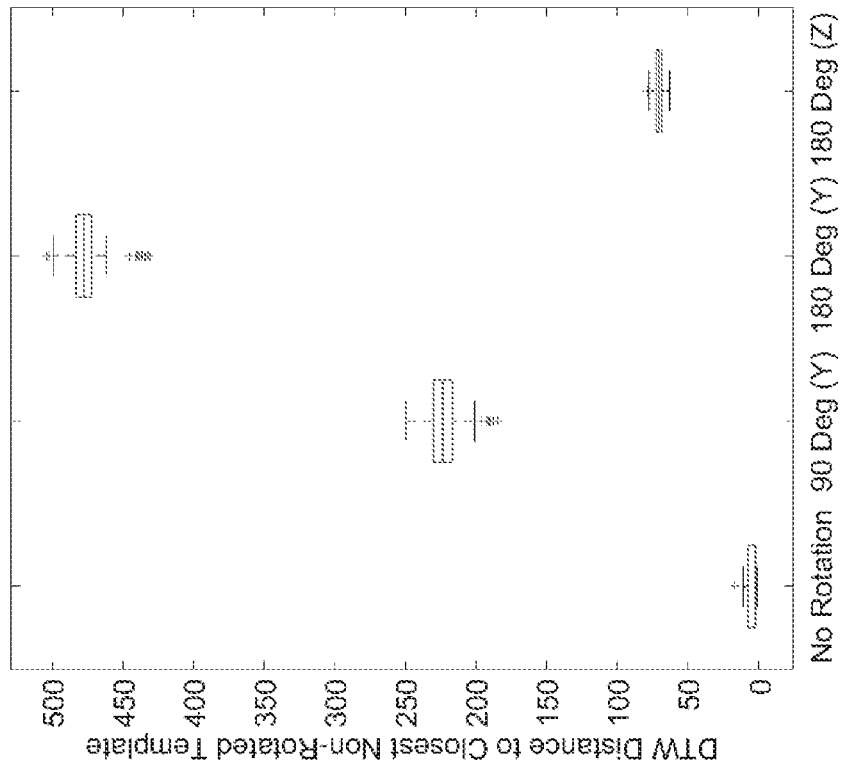

To verify that RSOI-DTW is invariant under a real rotation, that is a mis-orientation of the sensor, three of our participants completed a second trial with the sensor in four different orientations: no rotation, a 90° rotation about the medial-lateral axis, a 180° rotation about the medial-lateral axis, and a 180° rotation about the vertical axis. The 125 rotated signals were compared to the non-rotated signals using DTW and RSOI-DTW, and the resulting distances were used to recognize subjects by the rotated signals. As shown in FIG. 2, 1-nearest neighbor (1NN) recognition is perfect under RSOI-DTW but very poor under DTW. Further, RSOI-DTW distances were similar for all four orientations, as shown in FIGS. 3A and 3B. This strongly suggests that RSOI-DTW is RSO invariant in practice when used on inertial time series data.

Figure 4A:
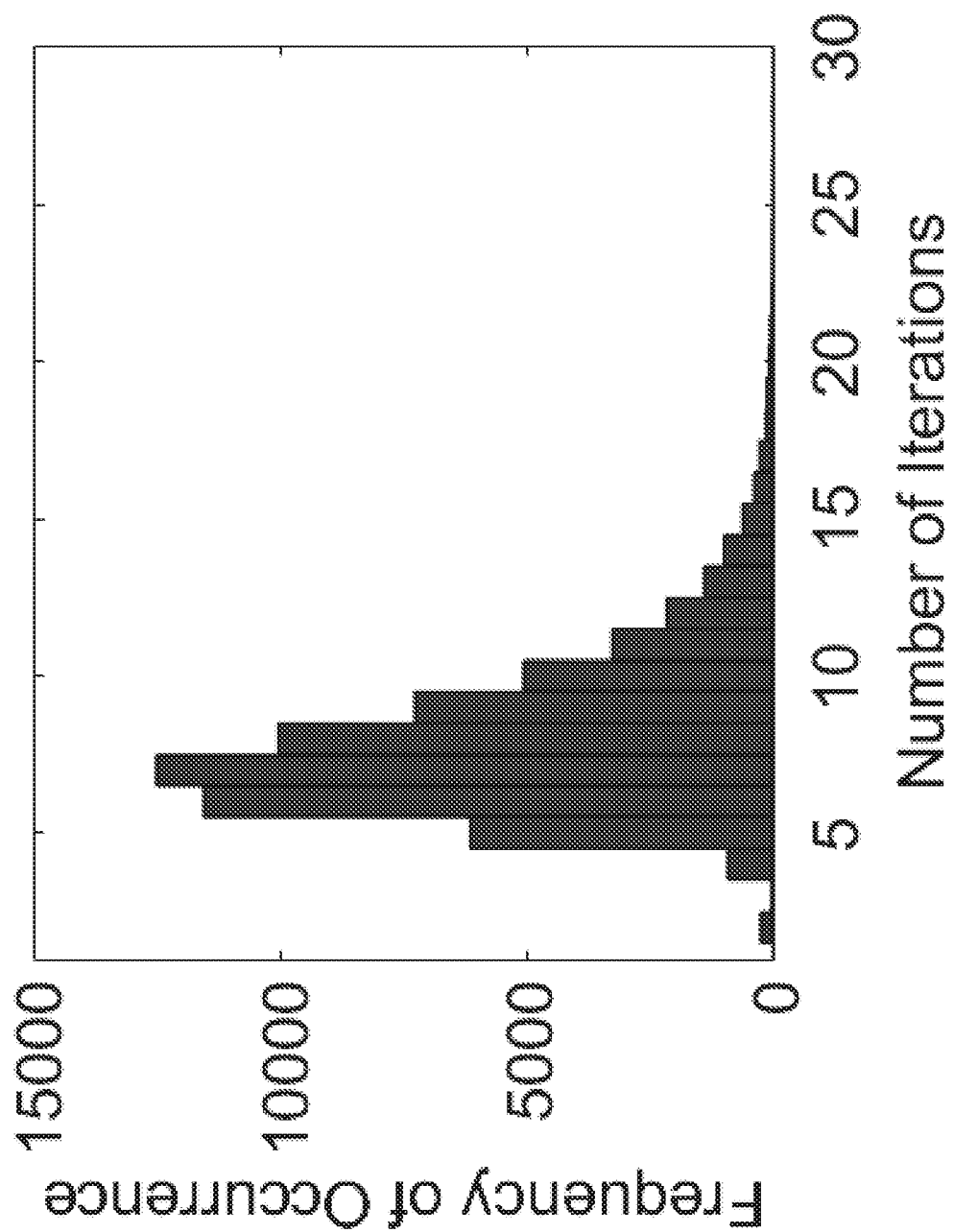

FIG. 4 contains histograms showing the convergence rate of RSOI-DTW when comparing (a) casual walking cycles to other casual walking cycles, and (b) fast walking cycles to casual walking cycles. In over 60,000 runs of RSOI-DTW per plot, the algorithm most often required 7 iterations, rarely required more than 20, and never more than 30. A strict convergence criterion was used: to ensure that the final warping path was locally optimal, we insisted that $d=d_{old}$ before convergence. As shown in Algorithm 1, each iteration includes one call of DTW and one call of the Procrustes algorithm.

Distinguishing Between Persons Using DTW and RSOI-DTW

For the gait recognition problem in all 21 subjects, 1NN classification is again used to match gait cycles to persons under the DTW and RSOI-DTW distances. In 1NN classification, a test cycle Y is classified as belonging to the owner of X, where X is the template cycle minimizing DTW(X, Y) or RSOI-DTW(X, Y).

FIG. 5 shows that gait recognition succeeds in the dataset not only with DTW, but also with RSOI-DTW. Out of 252 tested cycles, all 252 were classified correctly under the DTW distance, while a single misclassification occurred under the RSOI-DTW distance. When distinct, randomly chosen rotations were applied to each of the test cycles beforehand, DTW-based classification failed in most cases, as expected. On the other hand, the RSOI-DTW results were unchanged due to RSO invariance.

Figure 7B:
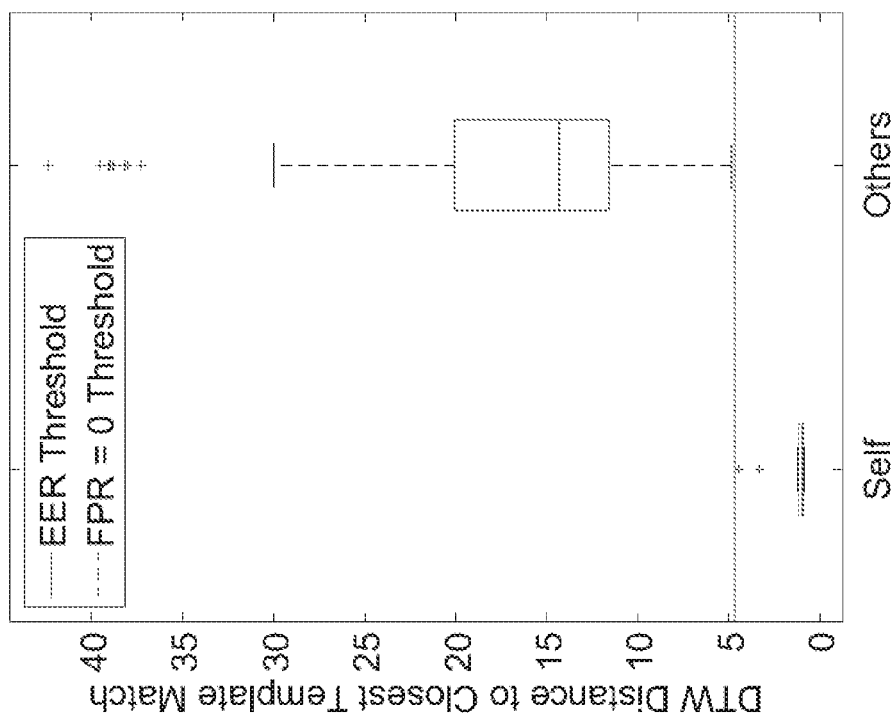
FIGS. 7A and 7B are graphical illustrations showing that threshold-based gait recognition is imperfect in subject 8 under RSOI-DTW because of two poorly matching casual gait cycles, but perfect in all but three of the other subjects.
Figure 7A:
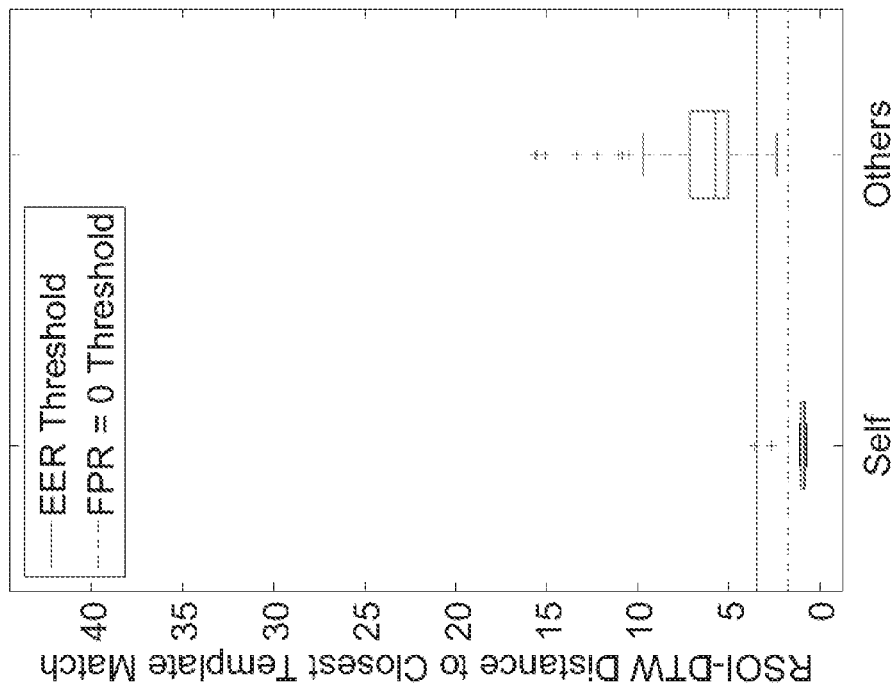

Gait recognition may also be treated as a decision problem: the algorithm must decide (YES/NO) whether a gait cycle of unknown origin belongs to a given person. As shown in FIGS. 7A and 7B, a threshold may be set on the best match between the tested cycle and the known subject's template cycles. If the distance for this match is below the threshold, the cycle is accepted, otherwise it is rejected. FIG. 6 summarizes the decision problem results in all subjects in terms of the equal error rate (EER), calculated by finding the threshold minimizing the difference between the false negative rate and the false positive rate, then taking their average for that threshold.

FIGS. 7A and 7B show decision problem results for subject 8, who had the worst EER (7.1%) under RSOI-DTW among all subjects because of two unusual, poorly matching cycles. The error rates are zero for all subjects under DTW and in 17 of 21 subjects under RSOI-DTW.

Detecting Simulated Pathology

Figure 8:
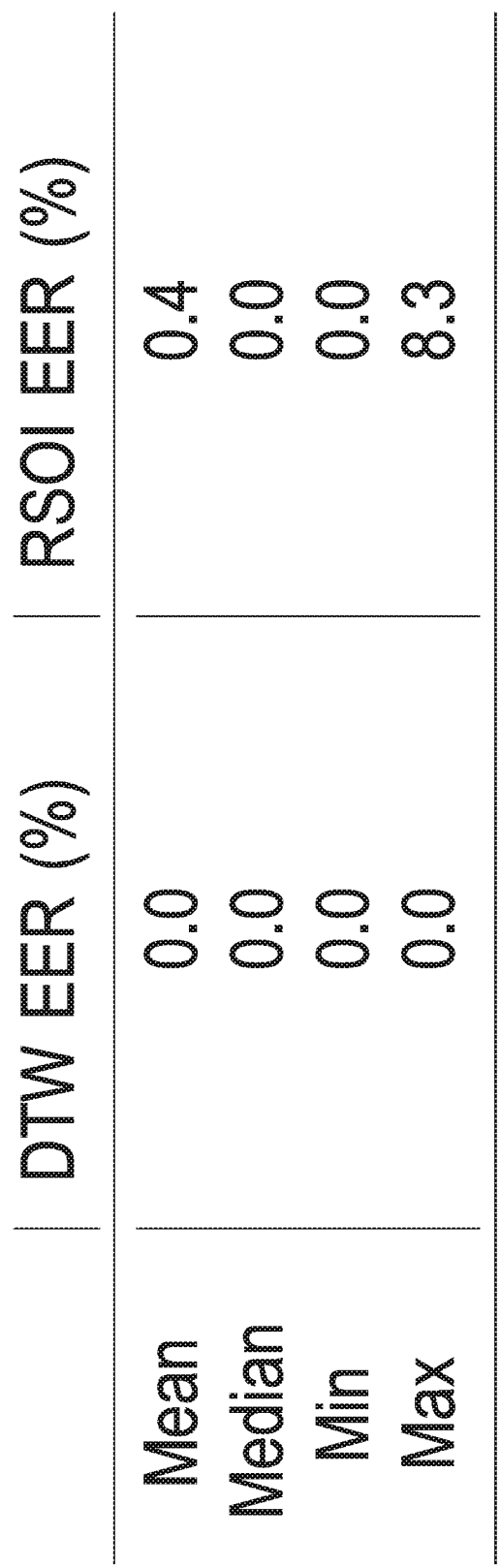
FIG. 8 is a table showing that simulated pathology can easily be distinguished from casual gait. This table summarizes the equal error rate (EER) for the decision problem with DTW and RSOI-DTW.

The pathology detection problem is similar to the gait recognition decision problem: the algorithm must decide (YES/NO) whether an unknown gait cycle represents normal gait or possible pathology. As before, a threshold is placed on the best match between the tested cycle and the known subject's template cycles. FIG. 8 shows that the simulated pathologies in our trial can be easily recognized in all subjects under both the DTW and RSOI-DTW distances: the EER is nonzero only in a single subject under RSOI-DTW. As before, only RSOI-DTW is capable of this accuracy in the presence of rotations, shifts, and scalings that may be present in a real-world use case.

FastWalking

An algorithm monitoring walking ability should be able to separate possible pathology from normal walking at any speed. Similarly, a gait recognition algorithm should accept cycles from a known individual regardless of speed, but reject cycles from other individuals. Amplitude and offset invariant DTW may be able to mitigate variability due to gait speed by warping and scaling cycles. Unfortunately, FIG. 9 shows that fast walking confuses the decision algorithm even under the RSOI-DTW distance. This table summarizes EER when distinguishing between normal walking, fast or slow, and the two simulated pathologies. Again, the casual walking cycles are used as templates. RSOI-DTW tends to improve performance because it can scale the fast gait cycles to match the casual cycles. Still, overall performance is poor under both measures.

Figure 10B:
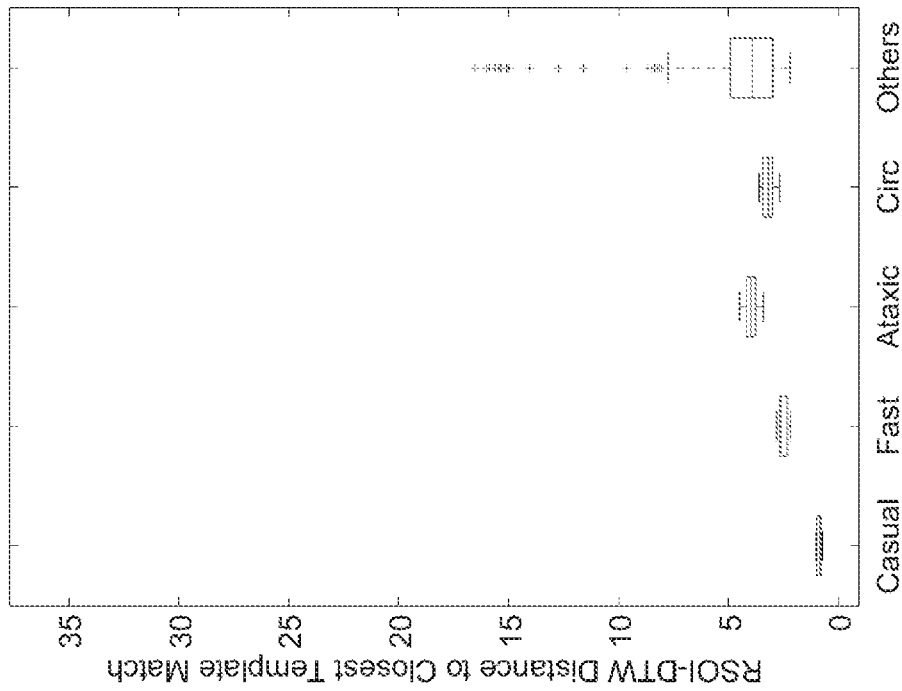
FIGS. 10A and 10B are graphical illustrations showing that fast gait confuses the pathology detection and gait recognition algorithms in subject 10 under DTW, but less so under RSOI-DTW. These figures show distances to the closest casual gait template cycle for several groups of cycles using DTW (FIG. 10A) and RSOI-DTW (FIG. 10B).
Figure 10A:
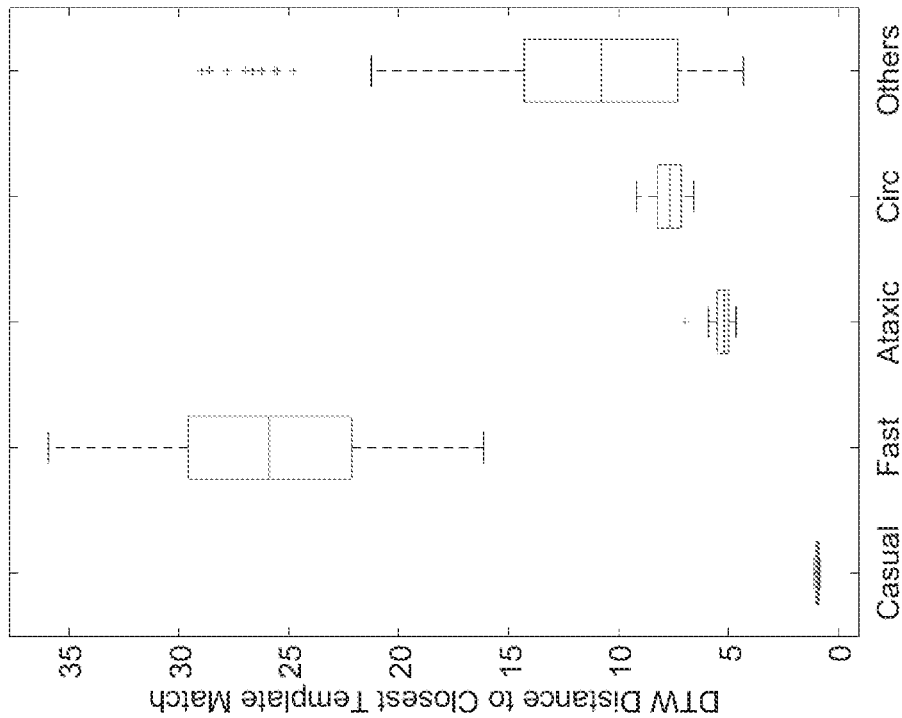
Figure 12:
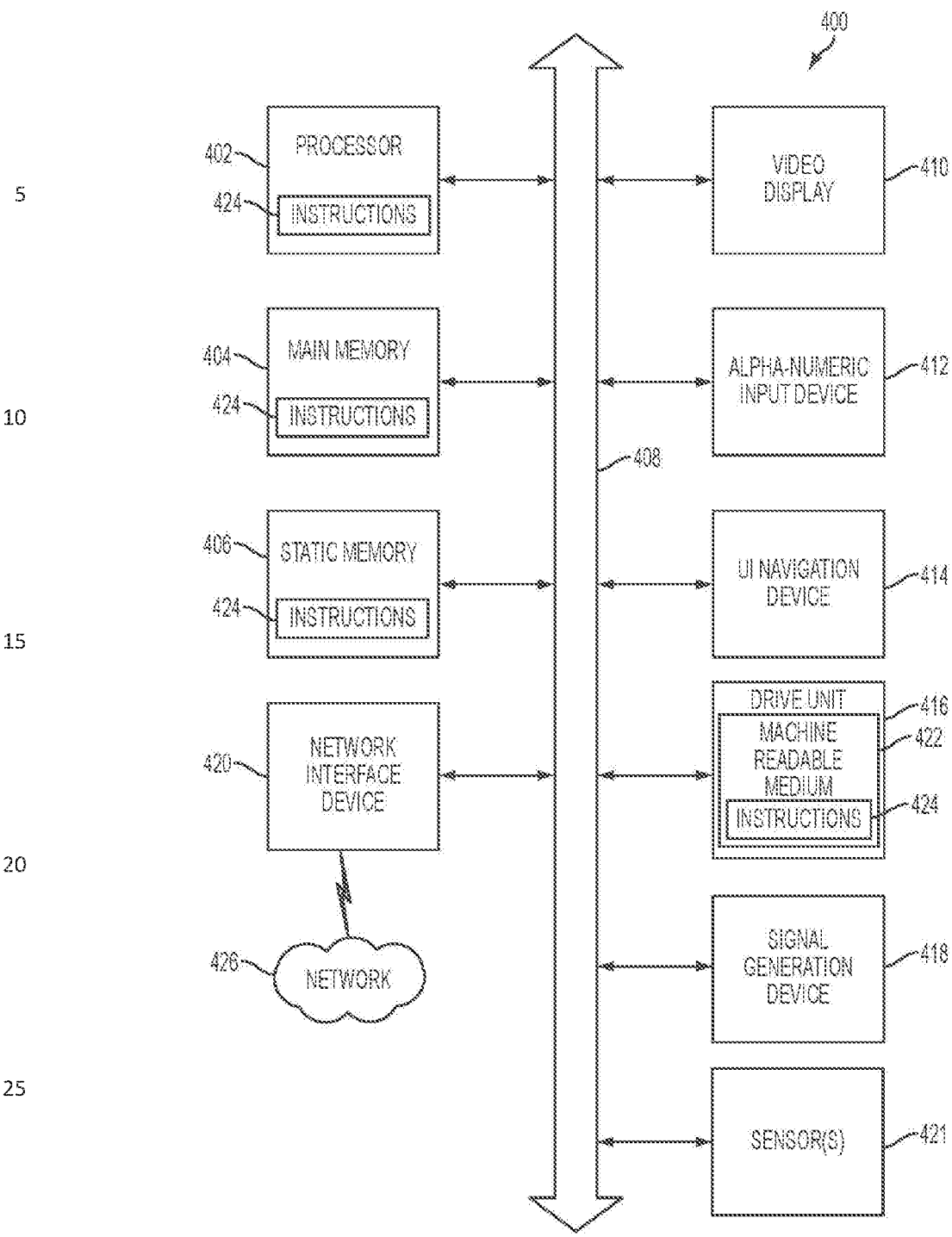
FIG. 12 is a block diagram illustrating an example of a machine upon which one or more aspects of embodiments of the present invention can be implemented.

FIGS. 10A and 10B illustrate this difficulty in subject 10: while RSOI-DTW dramatically lowers the distances between fast cycles and the template cycles compared to DTW, these distances are still large enough to confuse a pathology detection or gait recognition algorithm.

In light of this difficulty, either (1) walking speed must be consistent between all cycles, or (2) the template set must include cycles at a variety of speeds. To test the latter, fast walking cycles were added to the template set in each subject, with results shown in Table 5. With this modification, simulated pathology can again be distinguished from normal walking (casual or fast). Compared to the near perfect results in the previous section, however, the EER is high in a number of subjects. RSOI-DTW improves the EER in two subjects, but worsens it in others.

The focus is on gait recognition and pathology detection to highlight properties of RSOI-DTW advantageous for gait monitoring under real-world conditions. In the monitoring problem, however, gait patterns must be followed over time. This requires not only an appropriate similarity measure, but also a method for clustering cycles, tracking cluster progression, and summarizing it into an out-come measure. Clustering algorithms that accept an arbitrary distance metric, such as k-medoids or affinity propagation, would be an appropriate starting point.

As illustrated above, there is a trade-off when using RSOI-DTW instead of DTW. In most subjects, RSOI-DTW achieves rotation invariance while still clearly distinguishing subjects. In rare cases, however, its flexibility allows it to closely match cycles from different subjects. This confuses the decision algorithm more than the classification algorithm, because the former does not have information about the match distance to other subjects. To limit overfitting, the RSOI-DTW algorithm can be tailored to a particular use case, as mentioned above. When making this choice, there is a tradeoff between the sensitivity and specificity of the algorithm. If rotations are allowed, for example, there is a chance that the EER will increase. The results show that this unlikely, but possible. Further, there is a tradeoff in computational complexity when using RSOI-DTW. The algorithm converges quickly, but still must call DTW several times. Additional work is needed to explore how the size of the convergence criterion $\in$ affects the number of iterations. required by the algorithm.

RSOI-DTW solves the orientation problem, but not the gait speed problem. The distance between fast walking and casual walking is reduced, but still significant. As shown above, increasing the size and variety of the template set improves performance substantially. A further expansion of the template set may solve the problem.

Matching inertial time series can be broken into many sub-problems. One could find the gravitational vector, using it to partly correct the orientation, then adjust for sensor bias, finally using DTW to determine the optimal alignment, and so on. RSOI-DTW is attractive partly because it solves these issues at once with a single procedure. In our view, the RSO transformation is the most general affine transformation reasonable to use on inertial data; yet RSOI-DTW preserves the distinctive features required to distinguish persons and walking styles.

These results confirm that RSOI-DTW is an appropriate similarity measure for inertial gait data, and they support the proposed methodology for detection and monitoring of gait pathology. RSOI-DTW matches gait cycles despite incorrect sensor orientation, partly compensates for changes in gait speed, distinguishes the 21 participants almost perfectly, and detects the changes in walking style used in this trial.

Subsequent work will focus on using DTW and RSOI-DTW to monitor true pathology in both clinic and outpatient settings. In particular, we intend to monitor persons with multiple sclerosis while exercising to identify changes in walking patterns induced by fatigue.

Apparatus/System

A block diagram of an example machine 400 upon which one or more embodiments (e.g., discussed methodologies) can be implemented (e.g., run).

Examples of machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a stand-alone device or the machine 400 can be connected (e.g., networked) to other machines. In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410 (or audio unit), an alphanumeric input device 412 (e.g., a keyboard), and a user interface (UI) navigation device 414 (e.g., a mouse). In an example, the display unit 410, input device 412 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, image acquisition or recording device, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

Example

The theoretical properties of RSOI-DTW are established, and then the suitability of DTW and RSOI-DTW for pathology detection and monitoring is explored.

To evaluate DTW and RSOI-DTW as measures of walking ability, 21 healthy participants completed walking tests wearing an ActiGraph acclerometer. Following a brief overview of the relevant literature, the above discussion explains the walking test procedure in detail, reviews the DTW algorithm, and establishes the RSOI-DTW algorithm. The results from the walking tests are discussed above. This includes evidence that RSOI-DTW (1) converges quickly;

(2) achieves RSO invariance in practice; (3) retains the ability to distinguish persons despite its exibility in matching sequences; and (4) identities simulated pathology, suggesting that a trial with true pathology is warranted. The discussion above revisits these results in the presence of fast walking, highlighting the challenge posed by varying gait speed.

The subjects participated in the walking trial. Subjects wore a single ActiGraph accelerometer on their left hip, secured using an elastic belt with a pouch for the device. All subjects wore the same device. Each subject was asked to walk down a long corridor four times to demonstrate four different styles of gait: casual walking, fast walking, ataxic walking, and right leg circumduction. Ataxic walking is seen in persons with balance difficulties, characterized by a wide base and lateral swaying. Circumduction is the outward, circular swinging of one leg during its swing phase; it occurs when the leg is rigid or spastic at the knee and/or ankle joint. Subjects walked with each style in one direction for 40 steps, then turned, paused five seconds, and walked back with the next style. Each style was demonstrated before the trial, and subjects were given an opportunity to practice until comfortable.

Three subjects completed an additional trial in which they walked casually each time, but with four different sensor orientations. The data was manually divided by person and walking style and segmented into gait cycles, defined as the data between consecutive left heel strikes. There are prominent peaks in the accelerometer signal at the point of heel strike in all walking styles, making the heel strikes easy to identify. Subsequent processing using DTW and RSOI-DTW exploited these gait cycles.

REFERENCES

The following patents, applications and publications as listed below and throughout this document are hereby incorporated by reference in their entirety herein.

[1] P. Bours and R. Shrestha. Eigensteps: A giant leap for gait recognition. In 2010 2nd International Workshop on Security and Communication Networks (IWSCN), pages 1{6, May 2010.

[2] T.-W. Chen, M. Abdelmaseeh, and D. Stashuk. Affine and Regional Dynamic Time Warpng. arXiv: 1505.06531 [cs], May 2015. arXiv: 1505.06531.

[3] C. Chien, J. Y. Xu, H.-i. Chang, X. Wu, and G. J. Pottie. Model Construction for Human Motion Classification Using Inertial Sensors.

[4] M. Derawi, C. Nickel, P. Bours, and C. Busch. Unobtrusive User-Authentication on Mobile Phones Using Biometric Gait Recognition. In 2010 Sixth International Conference on Intelligent Information Hiding and Multimedia Signal Processing (IIH-MSP), pages 306{311, October 2010.

[5] D. W. Eggert, A. Lorusso, and R. B. Fisher. Estimating 3-D rigid body transformations: a comparison of four major algorithms. Machine Vision and Applications, 9(5-6):272{290, March 1997.

[6] J. Gong, P. Asare, J. Lach, and Y. Qi. Piecewise Linear Dynamical Model for Actions Clustering from Inertial Body Sensors with Considerations of Human Factors. In Proceedings of the 9th International Conference on Body Area Networks, BodyNets '14, pages 90{96, ICST, Brussels, Belgium, Belgium, 2014. ICST (Institute for Computer Sciences, Social-Informatics and Telecommunications Engineering).

[7] E. Keogh and C. A. Ratanamahatana. Exact indexing of dynamic time warping. Knowledge and Information Systems, 7(3):358{386, May 2004.

[8] M. Mancini, A. Salarian, P. Carlson-Kuhta, C. Zampieri, L. King, L. Chiari, and F. B. Horak. ISway: a sensitive, valid and reliable measure of postural control. Journal of NeuroEngineering and Rehabilitation, 9(1):59, August 2012.

[9] J. Mantyjarvi, M. Lindholm, E. Vildjiounaite, S.-M. Makela, and H. Ailisto. Identifying users of portable devices from gait pattern with accelerometers. In IEEE International Conference on Acoustics, Speech, and Signal Processing, 2005. Proceedings. (ICASSP'05), volume 2, pages ii/973{ii/976 Vol. 2, March 2005.

[10] R. Muscillo, S. Conforto, M. Schmid, P. Caselli, and T. D'Alessio. Classification of Motor Activities through Derivative Dynamic Time Warping applied on Accelerometer Data. In 29th Annual International Conference of the IEEE Engineering in Medicine and Biology Society, 2007. EMBS 2007, pages 4930{4933, August 2007.

[11] C. Nickel, M. Derawi, P. Bours, and C. Busch. Scenario test of accelerometer-based biometric gait recognition. In 2011 Third International Workshop on 02210-01 7 Security and Communication Networks (IWSCN), pages 15{21, May 2011.

[12] Y. Qiao and M. Yasuhara. Affine Invariant Dynamic Time Warping and its Application to Online Rotated Handwriting Recognition. In 18th International Conference on Pattern Recognition, 2006. ICPR 2006, volume 2, pages 905{908, August 2006.

[13] L. Rong, Z. Jianzhong, L. Ming, and H. Xiangfeng. A Wearable Acceleration Sensor System for Gait Recognition. In 2nd IEEE Conference on Industrial Electronics and Applications, 2007. ICIEA 2007, pages 2654{2659, May 2007.

[14] H. Sakoe and S. Chiba. Dynamic programming algorithm optimization for spoken word recognition. IEEE Transactions on Acoustics, Speech and Signal Processing, 26(1):43{49, February 1978.

[15] A. Salarian, F. Horak, C. Zampieri, P. Carlson-Kuhta, J. Nutt, and K. Aminian. iTUG, a Sensitive and Reliable Measure of Mobility. IEEE Transactions on Neural Systems and Rehabilitation Engineering, 18(3):303{310, June 2010.

[16] R. I. Spain, M. Mancini, F. B. Horak, and D. Bourdette. Body-worn sensors capture variability, but not decline, of gait and balance measures in multiple sclerosis over 18 months. Gait & Posture, 39(3):958{964, March 2014.

The invention claimed is:

1. A gait pathology detection and monitoring method, comprising:
    securing a personal activity tracking electronic device having an accelerometer sensor onto a leg of a user;
    detecting gait movement of the user during walking using the personal activity tracking electronic device;
    generating gait data of the user from the detected gait movement of the user during the walking;
    demonstrating at least one style of gait of the user when generating the gait data;
    processing the generated gait data using each of dynamic time warping (DTW) and rotation, scale, and offset (RSO) invariant dynamic time warping (RSOI-DTW), even when rotation of the accelerometer sensor is present during the detecting of the gait movement of the user during walking using the personal activity tracking device; and comparing results of the processing of the generated gait data using DTW and RSOI-DTW, respectively, to determine any gait recognition problem.

2. The method according to claim 1, further comprising applying at least one randomly chosen rotation amount to the accelerometer sensor prior to the detecting of the gait movement of the user during the walking using the personal activity tracking electronic device.

3. The method according to claim 1, further comprising applying gait recognition to the processed gait data to determine whether a gait cycle of unknown origin belongs to the user.

4. The method according to claim 1, further comprising determining whether a particular gait cycle represents the user's normal gait or a possible pathology.

5. The method according to claim 1, further comprising demonstrating four different styles of gait by the user when generating the user's gait data, including casual walking, fast walking, ataxic walking, and right leg circumduction.

6. The method according to claim 1, further comprising segmenting the user's gait data.

7. The method according to claim 6, wherein the user's gait data is segmented into gait cycles, defined as data between consecutive heel strikes of the user during detection.

8. The method according to claim 1, further comprising measuring changes in walkability of the user by detecting changes by comparing the user's current gait cycles against prior baseline gait cycles.

9. The method according to claim 8, wherein monitoring the user's walkability is measured on an ongoing basis.

10. A gait pathology detection and monitoring system, comprising:

a personal activity tracking electronic device having an accelerometer sensor, the personal activity tracking electronic device being configured to fit onto a leg of a user, detect gait movement of the user when walking, and generate, from the detected gait movement of the user, gait data of the user demonstrating at least one style of gait of the user; and an electronic apparatus configured to (a) receive the generated gait data of the user, (b) process the generated gait data using each of dynamic time warping (DTW) and rotation, scale, and offset (RSO) invariant dynamic time warping (RSOI-DTW), even when rotation of the accelerometer sensor is present during the detecting of the gait movement of the user when walking, and (c) compare results of the processing of the generated gait data using DTW and RSOI-DTW, respectively, to determine any gait recognition problem.

11. The system according to claim 10, wherein the electronic apparatus comprises a processor, a graphic processing unit, a memory and a bus connecting the memory to one or more of the processor and the graphic processing unit to allow communication between the memory and the one or more of the processor and the graphic processing unit.

12. The system according to claim 10, wherein the personal activity tracking electronic device and electronic apparatus are configured to communicate with each other.

13. The system according to claim 10, wherein the personal activity tracking device is configured to generate, from the detected gait movement of the user, gait data of the user demonstrating four different styles of gait by the user, including casual walking, fast walking, ataxic walking, and right leg circumduction.

\* \* \* \* \*